United States Patent

Sakai et al.

[11] 4,276,187
[45] Jun. 30, 1981

[54] OXIDATION-REDUCTION REAGENTS FOR A WET DESULFURIZATION PROCESS AND A PROCESS FOR PREPARING SAME

[75] Inventors: Katsuya Sakai, Yokohama; Ryuichi Mita; Toshio Kato, both of Kawasaki; Chojiro Higuchi, Kamakura; Hisamichi Murakami, Yokohama, all of Japan

[73] Assignee: Mitsui Toatsu Chemicals Incorporated, Tokyo, Japan

[21] Appl. No.: 26,934

[22] Filed: Apr. 4, 1979

[30] Foreign Application Priority Data

May 19, 1978 [JP] Japan ................... 53-58878

[51] Int. Cl.³ ............... C01B 17/02; C07C 143/42; A01N 1/00
[52] U.S. Cl. ............................. 252/186; 260/375; 260/376; 252/188; 423/573 R
[58] Field of Search ............... 260/376, 375, 573 R; 423/573 R; 252/186, 188

[56] References Cited

U.S. PATENT DOCUMENTS

| | | | |
|---|---|---|---|
| 1,917,421 | 7/1933 | Baumann et al. | 260/375 |
| 3,089,879 | 5/1963 | Sevves et al. | 260/376 |
| 3,280,154 | 10/1966 | Hopff et al. | 260/376 |
| 3,933,917 | 1/1976 | Schaffner et al. | 260/376 |

FOREIGN PATENT DOCUMENTS

149721 8/1973 Czechoslovakia.
149998 8/1973 Czechoslovakia.
150000 8/1973 Czechoslovakia.

Primary Examiner—Patrick Garvin
Assistant Examiner—Raymond K. Covington

[57] ABSTRACT

An oxidation-reducing reagent for a wet desulfurization process, which comprises (a) one or more compounds selected from the group consisting of salts of substituted anthraquinonesulfonic acids of the general formulas:

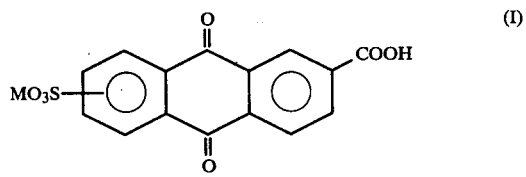

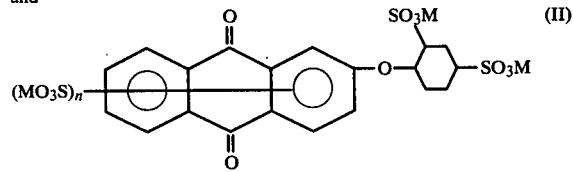

wherein M stands for a sodium atom, a potassium atom or an ammonium group, and n is an integer of 1 or 2, or (b) a mixture of a salt of anthraquinone-2,7-disulfonic acid and one or more compounds shown by the general formula (I) and/or (II), as well as a process for preparing the compounds of the general formulas (I) and (II).

4 Claims, 7 Drawing Figures

OXIDATION-REDUCTION REAGENTS FOR A WET DESULFURIZATION PROCESS AND A PROCESS FOR PREPARING SAME

BACKGROUND OF THE INVENTION

The present invention relates to an oxidation-reduction reagent comprising (a) one or more compounds selected from the group consisting of salts of substituted anthraquinonesulfonic acids of the general formula:

and wherein M stands for a sodium atom, a potassium atom or an ammonium group and n is an integer of 1 or 2, or (b) a mixture of a salt of anthraquinone-2,7-disulfonic acid and one or more compounds shown by the general formula (I) and/or (II), and also to a process for preparing these compounds.

In the past, it was reported that salts of 2-carboxyanthraquinonemonosulfonic acid shown by the general formula (I) was formed by sulfonation of 2-carboxyanthraquinone with 40% fuming sulfuric acid [A. G. Perkin, J. Chem. Soc. 65, 842 (1894)]. However, this reference nowhere gives a description of the use of this compound and salts thereof. No study has been reported since then on this compound. In recent years, it was disclosed that 2-carboxyanthraquinonedisulfonic acid is formed by heating 2-methylanthraquinone at 140°–170° C. with 30–50% fuming sulfuric acid and that this product can be used in place of anthraquinonedisulfonic acid in a wet desulfurization process according to the Stretford process (British Pat. No. 1,508,268).

Sulfonated products of 2-phenoxyanthraquinone which are shown by the general formula (II) are new compounds and have not been known hitherto.

In a wet desulfurization process, salts of anthraquinonedisulfonic acid are well known as useful oxidation-reduction reagents.

By the term "wet desulfurization process" is meant a process wherein a petroleum gas containing hydrogen sulfide, coal gas or a liquid hydrocarbon is brought into contact with a liquid containing an oxidation-reduction reagent capable of being reversibly oxidized or reduced, whereby the hydrogen sulfide is converted by oxidation into elementary sulfur and eliminated and, on the other hand, the oxidation-reduction reagent reduced by the oxidation of hydrogen sulfide is oxidized by contacting the reduced reagnet with air for regeneration, and this cycle is repeated for oxidation of hydrogen sulfide.

Among the wet desulfurization processes of the above mentioned type, one especially called "Stretford process" employs as an oxidation-reduction reagent a basic aqueous solution of (a) one or more anthraquinonedisulfonic acid or salts thereof or (b) a mixture of these with a compound of a metal capable of possessing two different kinds of valence, preferably a vanadate such as sodium metavanadate, optionally with a chelating agent such as potassium sodium tartarate or EDTA (Japanese Pat. Nos. 401,331, 405,170 and 405,171). In one of the most practical embodiments of this Stretford process where a basic aqueous solution of anthraquinonedisulfonates and sodium metavanadate is used as an oxidation-reduction reagent, the following reaction is surmised to take place ["Aromatics" 19, 53 (1967) published by Shadanhojin Nichon Hokozoku Kogyokai (Japan Aromatic Industry, Inc.)]:

$$2Na_2CO_3 + 2H_2S \rightarrow 2NaHS + 2NaHCO_3$$

$$4NaVO_3 + 2NaHS + H_2O \rightarrow Na_2V_4O_9 + 2S + 4NaOH$$

$$Na_2V_4O_9 + 2NaOH + 2ADA \rightarrow 4NaVO_3 + 2ADA^*$$

$$2ADA^* + O_2(air) \rightarrow 2ADA + 2H_2O$$

$$2NaHCO_3 + 2NaOH \rightarrow 2Na_2CO_3 + 2H_2O$$

In the above formulas, ADA stands for a salt of anthraquinonedisulfonic acid and ADA* for a leuco form of the salt of anthraquinonedisulfonic acid.

As is evident from the above reaction formulas, a salt of anthraquinonedisulfonic acid used in the Stretford process participates together with sodium metavanadate in the oxidation of hydrogen sulfide to elementary sulfur whereby the salt itself is reduced to a leuco form which is then oxidized to regenerate the salt when brought into contact with air. Heretofore, salts of anthraquinone-1,6-, -1,7- and -2,7-disulfonic acids are known to be effective as a salt of anthraquinonedisulfonic acid for the Stretford process. As a high water-solubility and a commercial availability at a low cost are required for practical use, however, salts of anthraquinonedisulfonic acids now practically utilizable are limited only to a salt of anthraquinone-2,7-disulfonic acid. Thus, the following serious problems arise in such situation.

Disulfonation of anthraquinone for preparing a salt of anthraquinone-2,7-disulfonic acid affords a mixture of almost equiamounts of anthraquinone-2,6- and -2,7-disulfonic acids. A salts of anthraquinone-2,6-disulfonic acid is sparingly soluble in a basic aqueous solution used in the Stretford process and is thus hardly utilizable for this process. If the salt of anthraquinone-2,6-disulfonic acid finds no useful application, it will become extremely difficult to supply a salt of anthraquinone-2,7-disulfonic acid at a low cost for the Stretford process. In addition, the use of anthraquinone-2,6-disulfonic acid is limited to the preparation of specific dye intermediates, whereas the Stretford process distinguished by its extremely high desulfurization ratio permitting the effect that the content of the remaining hydrogen sulfide in the refined gas treated according to this process is extremely low is now being adopted gradually widely. Thus, a significant inbalence in utility is found between the 2,6-disulfonic acid and the 2,7-disulfonic acid, and there is a great demand for a reagent capable of substituting itself for the 2,7-disulfonic acid without such limitation.

To fill the demand, 2-carboxyanthraquinonedisulfonic acids were proposed which are obtained by heating 2-methylanthraquinone with fuming sulfuric acid at a high temperature (DOS. No. 2,639,365 and British Pat. No. 1,508,268). According to the present inventors' experiments, however, it has been found that 2-carboxyanthraquinonedisulfonic acids obtained in the above mentioned manner are in the form of a complex mixture comprising at least 7 isomers and decomposition products having indefinite structures and that as will be described hereinafter, a difficult problem arises in the formation of by-products which are inferior in solubility in a concentrated inorganic brine containing a base, the solubility being one of the properties required for oxidation-reduction reagents for use in a wet desulfurization process.

It is necessary that oxidation-reduction reagents used for a wet desulfurization process, especially the Stretford process be furnished with such properties and economical merits as will be itemized below.

(1) Good solubility in an absorbing liquid used in the wet desulfurization process (In the wet desulfurization process, a weakly alkaline absorbing liquid is circulated in the system for the treatment of a gas containing hydrogen sulfide whereby the hydrogen sulfide is not oxidized to elemental sulfur at a conversion rate of 100% and a part of the hydrogen sulfide is oxidized to thiosulfates and sulfates or converted into rhodanides when cyanides are present in the feed gas. Since these by-products are built up in the absorbing liquid, the concentration of inorganic salts in the absorbing liquid will reach a level as high as 300–400 g/l after a continuous run for a long period of time. Thus, a practically utilizable oxidation-reduction reagent should possess a good solubility even in a highly concentrated solution of inorganic salts.)

(2) Moderate oxidation-reduction capacity and rate (As is evident from the reaction formulas previously given, a combination of sodium vanadate and anthraquinonesulfonates constructs an oxidation-reduction system. Consequently, the anthraquinonesulfonates used as catalyst are required to have a moderate oxidation-reduction capacity and rate).

(3) Minimum consumption (As the oxidation-reduction cycle is repeated in the absorbing liquid, it is unavoidable that the catalyst is gradually consumed by side-reactions. However, the consumption of the catalyst should be as minimum as possible.)

(4) Low toxicity and easiness in the treatment of waste liquor (5) In the preparation of the oxidation-reduction reagents, the formation of no by-product which is sparingly soluble and cannot be used for the Stretford process (6) Easiness in substitution for anthraquinone-2,7-disulfonate used hitherto for the Stretford process (7) Possibility of the conjoint use with anthraquinone-2,7-disulfonate for facilitating the substitution work stated in item (6)

(8) Possibility of producing the end product of high purity as simple in the steps as possible.

As a result of our researches made for synthesis of a great number of anthraquinonesulfonates with a view to developing an oxidation-reduction reagent which can fully satisfy the foregoing requirements and for testing of the catalytic performance of these anthraquinonesulfonates in the Stretford process, it has now been found that the compounds of the above general formulas (I) and (II) fully satisfy the foregoing requirements and exhibit an excellent catalytic performance. The present invention has been accomplished on the basis of the above finding.

SUMMARY OF THE INVENTION

Accordingly, an object of the invention is to provide an oxidation-reduction reagent containing one or more anthraquinone derivatives useful for a wet desulfurization process.

Another object of the invention is to provide a process for the preparation of compounds of the formula:

wherein M stands for a sodium atom, a potassium atom or an ammonium group.

Further object of the invention is to provide a process for the preparation of compounds of the formula:

wherein M stands for a sodium atom, a potassium atom or an ammonium group and n is an integer of 1 or 2.

Other objects, features and advatages of the invention shall appear more fully from the following description and from the accompanying drawings.

DETAILED DESCRIPTION OF THE INVENTION

According to an embodiment of the present invention, compounds of the general formulas (I) and (II) are prepared by the method described hereinafter. The preparation of the compounds is carried out with only a few reaction steps, using easily available starting materials, whereby no difficult problem arises unlike the case of preparing anthraquinone-2,7-disulfonates where a difficult problem arises in the treatment of sparingly soluble isomers formed as by-products. The compounds of the general formulas (I) and (II) are in the form of a mixture of two or more isomers, but they are superior, as shown in Table 1 below, in solubility in an alkaline solution of inorganic salts having a high concentration to anthraquinone-2,7-disulfonates.

TABLE 1

| Compound | Solubility (g/l, 25° C.) | | | |
|---|---|---|---|---|
| | 20g Na$_2$CO$_3$ + 300g Na$_2$S$_2$O$_3$ in 1 liter of water | 20g Na$_2$CO$_3$ + 300g NaSCN in 1 liter of water | Mixed* aqueous solution | Water |
| Sodium anthraquinone-2,6-disulfonate | <1 | <1 | <1 | 39 |
| Sodium anthraquinone-2,7-disulfonate | 10 | 8 | 5 | 305 |
| Sodium 2-carboxy-anthraquinonemono-sulfonate | 38 | 25 | 15 | 12 |
| Sodium 2-phenoxy-anthraquinonetri-sulfonate | >200 | >100 | >100 | >400 |
| Sodium 2-phenoxy-anthraquinonetetra-sulfonate | >300 | >200 | >200 | >600 |

*An aqueous solution containing 20 g/l of sodium carbonate, 50 g/l sodium sulfate, 100 g/l of sodium thiosulfate and 150 g/l of sodium thiocyanate.

Referring to Table 1, sodium 2-carboxyanthraquinonemonosulfonate of the general formula (I) is soluble in pure water to afford a weakly acidic solution of pH 3-4 and shows a solubility of 12 g/l but shows as disodium salt a solubility of 200 g/l or more in a neutral or weakly alkaline solution. Thus, it was indeed an unexpectedly noticeable discovery that a monosulfonate of a carboxyanthraquinone was superior in solubility to anthraquinonedisulfonates. It is also surprising that 2-carboxyanthraquinonemonosulfonate of the general formula (I) is considered, as described hereinafter, to be a mixture of 2-carboxyanthraquinone-6-sulfonate and 2-carboxyanthraquinone-7-sulfonate but both isomers are easily soluble in an alkaline solution of inorganic salts having a high concentration unlike the cases of anthraquinone-2,6-disulfonate and anthraquinone-2,7-disulfonate.

Another group of anthraquinone derivatives synthesized according to the process of this invention, i.e. 2-phenoxyanthraquinonetri- and -tetrasulfonates of the general formula (II) possess significantly high solubilities in an aqueous solution of inorganic salts having a high concentration as shown in Table 1.

It is easily surmised that compounds of the general formulas (I) and (II) are reversibly oxidized or reduced since they have an anthraquinone skeleton. Easiness in oxidation-reduction of these compounds is evaluated by their standard oxidation-reduction potential and their oxidation and reduction rates. Thus, a test was made for these compounds to measure (a) the time required for being reduced to the leuco form by sodium vanadite (Na$_2$V$_4$O$_9$), (b) the time required for being oxidized to regenerate the quinone form and (c) standard oxidation-reduction potentials $E_o$, the results of measurement being shown in Table 2 below.

TABLE 2

| Compound | Reaction Rates | | |
|---|---|---|---|
| | Time required for reduction to the leuco form* | Time required for oxidation to regenerate the quinone form** | Standard oxidation-reduction potential $E_o$ (25° C.) |
| Sodium anthraquinone-2,7-disulfonate | 5 minutes | 15 minutes | 0.29 V |
| Sodium 2-carboxy-anthraquinonemono-sulfonate | 5 minutes | 15 minutes | 0.29 V |
| Sodium 2-phenoxy-anthraquinonetri-sulfonate | 5 minutes | 15 minutes | 0.27 V |
| Sodium 2-phenoxy-anthraquinonetetra-sulfonate | 5 minutes | 15 minutes | 0.28 V |

*In nitrogen atmosphere, sodium vanadite (0.02 mol/l) was reacted at 38° C. with a given anthraquinonesulfonate (0.04 mol/l) in the presence of sodium hydroxide (0.04 mol/l) in an alkaline aqueous solution whereby the time required for reducing the anthraquinone compound to the leuco form (the corresponding hydroquinone compound) was determined by measuring the absorption bands in the visible region. Below are the maximum absorption wave lengths of the leuco forms.

| Sodium leuco-anthraquinone-2,7-disulfonate | 450nm |
| Sodium leuco-2-carboxyanthraquinonemono-sulfonate | 451nm |
| Sodium leuco-2-phenoxyanthraquinonetri-sulfonate | 439nm |
| Sodium leuco-2-phenoxyanthraquinonetetra-sulfonate | 448nm |

**Air was absorbed at 38° C. in an aqueous solution containing a given leuco-anthraquinonesulfonate (0.04 mol/l) and sodium hydroxide (0.08 mol/l) under agitation whereby the time required for finishing the air-absorption was measured.

As is evident from Table 2, sodium 2-carboxyanthraquinonesulfonate, sodium 2-phenoxyanthraquinonetrisulfonate and sodium 2-phenoxyanthraquinonetetrasulfonate are very similar in oxidation-reduction characteristics to sodium anthraquinone-2,7-disulfonate.

In veiw of the solubility and oxidation-reduction characteristics above described, the anthraquinone compounds of the general formulas (I) and (II) are expected to exert an equivalent performance to anthraquinone-2,7-disulfonate as an oxidation-reduction reagent used for the Stretford process. In fact, these anthraquinone compounds were proved to attain the expected results in a test for absorbing hydrogen sulfide according to the Stretford process using an absorbing liquid for desulfurization to which these anthraquinone compounds had been added. The results of the test are given in Examples 11-17. The compounds of the general formulas (I) and (II) exerted in the Stretford process an equivalent desulfurization performance to anthraquinone-2,7-disulfonates. In other words, these anthraquinone compounds are quite equivalent to or somewhat better than anthraquinone-2,7-disulfonate in elimination rate of hydrogen sulfide (desulfurization ratio), a conversion rate of the absorbed hydrogen sulfide to elemental sulfur and a concentration of the residual hydrogen sulfide in the refined gas.

Below are technical advantages of the oxidation-reduction reagents of the present invention obtainable when used for the Stretford process.

In case the anthraquinone compounds of this invention are used in place of anthraquinonedisulfonates in the Stretford process, no special modification is necessary for the pH value and composition of the alkaline aqueous solution except that a part or all of the anthraquinonedisulfonates in the alkaline aqueous solution is replaced by an equimolar amount of the compounds of this invention. An aqueous solution containing about 0.1% or more of the compounds of this invention singly or as a mixture with anthraquinonedisulfonates is first prepared and then ammonia and an alkali metal carbonate are added to the solution to prepare an alkaline aqueous solution having a pH value of at least 7, preferably 8.5–9.5 which is utilizable for the Stretford process. A compound of a metal having at least two different valences, for example, sodium metavanadate is preferably added in a concentration of 1/1000–1/20 mol/l to the alkaline aqueous solution. If necessary, a chelating agent such as potassium sodium tartarate or ethylenediaminetetraacetates may be used jointly.

In case the compounds of this invention are used in place of anthraquinonedisulfonates, the following further advantages are achieved. When anthraquinone-2,7-disulfonic acid is prepared, an almost equiamount of anthraquinone-2,6-disulfonic acid also forms which is unsuited for the Stretford process because of its very poor solubility. Contrary to this, the compounds of this invention are free of sparingly soluble isomers and can thus be employed wholly for the Stretford process.

In the Stretford process wherein the alkaline aqueous solution is circulated in the system for a long period of time, there arises a problem in the point that a large amount of inorganic salts such as sodium sulfate, sodium thiosulfonate and sodium thiocyanate is built up gradually in the solution whereby anthraquinonedisulfonates may easily be salted out and discharged out of the system together with elemental sulfur. However, in case of using the compounds of this invention which, as described above, show very good solubility in the alkaline aqueous solution of inorganic salts, any loss of the compounds caused by salting-out during the recycling operation is very slight and almost negligible.

The compounds of this invention can be used in the alkaline aqueous solution at an increased concentration, taking advantage of their excellent solubility in the solution, as compared with the case of using anthraquinone-2,7-disulfonate whereby the disulfurization efficiency is enhanced to attain more complete removal of hydrogen sulfide so that the size of apparatus may be made smaller.

On the other hand, the compounds of this invention are very similar in oxidation-reduction characteristics to anthraquinone-2,7-disulfonates and can thus be used under the same conditions as adopted for the use of anthraquinone-2,7-disulfonates. Accordingly, it is an additional merit of the present invention that the apparatus used in the conventional art anthraquinone-2,7-disulfonates can directly be used for the compounds of this invention without modifying the operation conditions for the reactions or reconstructing the apparatus. If the type of reagent is changed, it may be unnecessary to substitute the a new reaction liquid for the existing reaction liquid since the compounds of this invention can be used equivalently as a mixture with anthraquinone-2,7-disulfonates. Such purpose can be attained merely by varying the sort of the reagents to be supplied to the reaction liquid to compensate for the consumed quantity of the reagents.

Given below is a detailed description on the process for preparing the compounds of the general formulas (I) and (II).

2-Carboxyanthraquinonemonosulfonates of this invention are shown by the general formula (I):

wherein M stands for a sodium atom, a potassium atom or an ammonium group, and are obtained by heating benzophenone-2,4-dicarboxylic acid, benzophenone-2,5-dicarboxylic acid or 2-(p-carboxybenzoyl)benzoic acid with a dehydrating agent and a sulfonating agent without isolating 2-carboxyanthraquinone formed as an intermediate product.

On example for the preparation of each of the aforementioned starting materials is shown briefly as follows: Benzophenone-2,4-dicarboxylic acid is obtained by a Friedel-Crafts reaction between trimellitic anhydride and benzene. Benzophenone-2,5-dicarboxylic acid is obtained by oxidizing the methyl group of 2-benzoyl-4-methyl-benzoic acid. 2-(p-carboxybenzoyl)benzoic acid is obtained by oxidizing the methyl group of 2-(p-methylbenzoyl) benzoic acid.

Fuming sulfuric acid, sulfuric acid, sulfur trioxide, polyphosphoric acid and phosphorus pentoxide are illustrative of the dehydrating agent used for the cyclization reaction of benzophenone-2,4-dicarboxylic acid, benzophenone-2,5-dicarboxylic acid or 2(p-carboxybenzoyl) benzoic acid and for the subsequent sulfonation reaction, while fuming sulfuric acid, sulfur trioxide and chlorosulfonic acid are illustrative of the sulfonating agent. In case of using these dehydrating agent and sulfonating agent, the cyclization reaction and the sulfonation reaction may be carried out in the presence of an inert solvent such as liquid sulfur dioxide, sulfolane or a halogenated hydrocarbon. Usually, however, it is of advantage that the dehydrating agent and/or sulfonating agent also functions as a solvent.

The reactions are performed either by heating the afore-mentioned starting material in the dehydrating agent to effect the cyclization reaction and successively adding the sulfonating agent to the reaction liquid and heating the mixture to effect the sulfonation reaction or by heating the starting material in a mixture of the dehydrating agent and the sulfonating agent to effect the cyclization reaction followed by the sulfonation reaction.

Industrially, the cyclization and sulfonation reactions are carried out especially advantageously by using fuming sulfuric acid. Thus, 2-carboxyanthraquinonemonosulfonic acid aimed at can be obtained by merely heating benzophenone-2,4-dicarboxylic acid, benzophenone-2,5-dicarboxylic acid or 2-(p-carboxybenzoyl) benzoic acid in fuming sulfuric acid, thus affording such a merit that a troublesome operation as in the case of using different dehydrating agent and sulfonating agent is not necessary. In this case, the concentration of free $SO_3$ in the fuming sulfuric acid is within the range from 0% (i.e. 100% sulfuric acid) to 80%. If the concentration is lower than the above range (or in case of using sulfuric acid lower in concentration than 100% sulfuric acid), the cyclization reaction of benzophenone-2,4-dicarboxylic aicd, benzophenone-2,5-dicarboxylic acid or 2-(p-carboxybenzoyl) benzoic acid will proceed but the sulfonation reaction of 2-carboxyanthraquinone to 2-carboxyanthraquinonemonosulfonic acid will hardly proceed. On the other hand, if the concentration exceeds 80%, handling of such fuming sulfuric acid will become troublesome and sidereactions permitting the formation of impurities will tend to take place. For practical operations, the use of such fuming sulfuric acid as having a $SO_3$ concentration of 5–60%, preferably 20–60% is desirable. The amount of fuming sulfuric acid varies according to the concentration of free $SO_3$ contained therein but usually is 5–100 parts (the part is shown herein by weight) per 10 parts of the starting benzophenone-2,4-dicarboxylic acid, benzophenone-2,5-dicarboxylic acid or 2-(p-carboxybenzoyl) benzoic acid. Considering the reaction operations, the use of fuming sulfuric acid in an amount within the range of 5–100 parts, preferably 15–50 parts per 10 parts of the starting material is especially convenient.

The reactions are performed by adding benzophenone-2,4-dicarboxylic acid, benzophenone-2,5-dicarboxylic acid or 2-(p-carboxybenzoyl)benzoic acid to the fuming sulfuric acid, gradually elevating the temperature of the mixture with stirring and maintaining the temperature at 80°–200° C. for 1–40 hours, preferably 2–20 hours and more preferably 5–15 hours. Completion of the cyclization and sulfonation reactions can easily be noted, for example, by disappearance of 2-carboxyanthraquinone spots in a thin layer chromatography of the reaction liquid [thin layer sheet: Spot film silica gel-f available from Tokyo Kasei Kogyo KK, Japan; developing liquid: n-butanol-ethanol-0.5 N-aqueous ammonia solution (6:2:3 in volume ratio)].

In the reactions, an alkali metal sulfate such as sodium sulfate or potassium sulfate may be added to prevent oxidation of the anthraquinone nucleus. After completion of the reactions, the reaction liquid is diluted with water and the precipitate formed is collected by filtration or sodium sulfate, potassium sulfate or the like salt is added to salt-out the product whereby 2-carboxyanthraquinonemonosulfonate aimed at can be obtained in a high yield.

Figure 1:
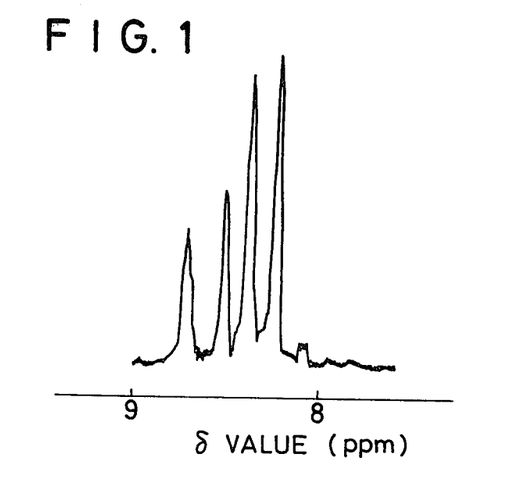
FIG. 1 is a proton-NMR-absorption spectrograph of sodium 2-carboxyanthraquinonemonosulfonate.

The fact that in the resultant 2-carboxyanthraquinonemonosulfonate, the sulfonate group has been introduced into the 6- or 7-position thereof is evident from a proton-NMR-absorption spectrograph of this compound. FIG. 1 shows a proton-NMR-absorption spectrum (solvent:DMSO, measuring temp.:room temperature) of sodium 2-carboxyanthraquinonemonosulfonate obtained in Example 1.

In the compounds of the formulas (III) and (IV):

absorption of protons a, b is detected in 8.36 ppm(2H), absorption of proton c in 8.71 ppm(1H), absorption of protons d, e in 8.24 ppm (2H) and absorption of proton f in 8.51 ppm (1H). Thus, it is confirmed that the sulfonate group has been introduced into the 6- or 7-position of the product.

In a high speed liquid chromatography of this product, two components having retention times different from each other were detected. This fact obviously shows that the 2-carboxyanthraquinonemonosulfonate obtained in the present invention is a mixture of 2-carboxyanthraquinone-6-sulfonate and 2-carboxyanthraquinone-7-sulfonate of the above formulas (III) and (IV), respectively.

As 2-carboxyanthraquinonemonosulfonic acid is a dibasic acid, the product can be isolated in either form of the free acid, the acidic salt (2-carboxyanthraquinonemonosulfonate) and the neutral salt (e.g. disodium salt or dipotassium salt). The free acid and these salts can equivalently be used as an oxidation-reduction reagent for the Stretford process. As the reaction liquid used in the Stretford process is alkaline and has a pH value of 8.5–9.5, 2-carboxyanthraquinonemonosulfonic acid is present therein as the neutral salt, i.e. in the form of disodium salt, regardless of what form of the product is used. Any counter ion can be selected unless it forms a sparingly soluble salt in the working solution for the Stretford process. Either of an alkali metal ion and ammonium ion is preferably selected.

The isolation of the product as free acid necessitates precipitation and filtration of the free acid from an acidic solution having a high acid concentration. Thus, such operation is economically disadvantageous as the materials constructing the apparatus must be resistant to a strongly acidic solution. The isolation of the product as neutral salt necessitates the use of an inorganic salt such as sodium sulfate or potassium sulfate at a high concentration for salting-out and fails to warrant a high yield since the product has a high solubility in a neutral to weakly acidic water. For convenience of preparation of the product, the isolation of the product as acidic salt is desirable and is easily conducted since the acidic salt has a relatively low solubility and is precipitated only by adding a small amount of an inorganic salt to an acidic solution of the product.

Hitherto, the oxidation of a 2-alkylanthraquinone [e.g. Whitmore, J. Am. Chem. Soc. 51, 856 (1924)] has been known as a general method for preparing 2-carboxyanthraquinone. Also known as a method for preparing 2-carboxyanthraquinone is a process wherein benzophenone-2,4-dicarboxylic acid is heated in sulfuric acid (British Pat. No. 1,304,538).

However, the method wherein a 2-alkylanthraquinone is oxidized is attended with a problem of environmental pollution caused by oxidizers. In addition, this method necessitates isolation of 2-carboxyanthraquinone after oxidation for subjecting it to the successive sulfonation, thus making the step complicated. The method wherein benzophenone-2,4-dicarboxylic acid is heated in sulfuric acid also necessitates isolation of 2-carboxyanthraquinone and is thus disadvantageous in complexity of the steps.

In contrast to these known methods involving drawbacks, the process of this invention is advantageous in that after cyclization of benzophenone-2,4-dicarboxylic acid, benzophenone-2,5-dicarboxylic acid or 2-(p-carboxybenzoyl)benzoic acid, the step for isolating the resulting 2-carboxyanthraquinone is unnecessary so that the route from the above starting material to 2-carboxyanthraquinonemonosulfonic acid may be simplified and the amount of industrial effluents becomes smaller.

Furthermore, the process of this invention has such a merit that since 2-carboxyanthraquinonemonosulfonate obtained according to this invention consists, as described above, of only two isomers of 2-carboxyanthraquinone-6-sulfonate and 2-carboxyanthraquinone-7-sulfonate and is free of other isomers and decomposition products, the product of such high purity facilitates control of the preparation conditions and analysis of the product on preparation or practical use.

The other class of anthraquinone compounds of the present invention is shown by the general formula (II):

wherein M stands for a sodium atom, a potassium atom or an ammonia group and n is an integer of 1 or 2. More particularly, the other class of anthraquinone compounds is comprised of 2-phenoxyanthraquinonetrisulfonates of the general formula (V):

wherein M has the same meaning as given in the general formula (II), 2-phenoxyanthraquinonetetrasulfonates of the general formula (VI):

wherein M has the same meaning as given in the general formula (II), and a mixture of these 2-phenoxyanthraquinonetrisulfonates and 2-phenoxyanthraquinonetetrasulfonates.

According to one embodiment of the process of this invention for preparing the 2-phenoxyanthraquinonepolysulfonates, 2-phenoxyanthraquinone is sulfonated under heating with a sulfonating agent.

2-phenoxyanthraquinone used as the starting material can easily be obtained by reacting sodium anthraquinone-2-sulfonate with potassium phenolate at 200° C. or by reacting 2-chloroanthraquinone with phenol in the presence of sodium hydroxide. This starting material is obtained also by treating 2-(p-phenoxybenzoyl) benzoic acid with a dehydrating agent such as phosphorus pentoxide, polyphosphoric acid or aluminum chloride to effect dehydration.

According to another embodiment of the process of this invention for preparing the 2-phenoxyanthraquinonepolysulfonates, 2-(p-phenoxybenzoyl) benzoic acid is heated with a dehydrating agent and a sulfonating agent. In this case, the reaction proceeds according to the route shown by the reaction formulas (1):

2-(p-phenoxybenzoyl) benzoic acid used as the starting material in this process is obtained by the Friedel-Crafts reaction between phthalic anhydride and diphenyl ether.

Examples of the sulfonating agent used in this invention for sulfonating 2-phenoxyanthraquinone include fuming sulfuric acid, sulfur trioxide and chlorosulfonic acid. Examples of the dehydrating agent used in this invention together with a sulfonating agent for dehydrocyclization and sulfonation of 2-(p-phenoxybenzoyl) benzoic acid include fuming sulfuric acid, sulfuric acid, sulfur trioxide, polyphosphoric acid and phosphorus pentoxide, while examples of the sulfonating agent in this embodiment include fuming sulfuric acid, sulfuric acid, sulfur trioxide and chlorosulfonic acid. The use of fuming sulfuric acid, sulfuric acid or sulfur trioxide which functions as both dehydrating agent and sulfonating agent is industrially advantageous. In either process wherein 2-phenoxyanthraquinone is used as starting material and wherein 2-(p-phenoxybenzoyl) benzoic acid is used as starting material, the reaction may be carried out in a solvent inert to the dehydrating agent and the sulfonating agent, for example, in liquid sulfur dioxide or in a halogenated hydrocarbon. Usually, however, the use of the dehydrating agent and/or sulfonating agent functioning also as solvent is advantageous.

In case 2-phenoxyanthraquinonetrisulfonates are synthesized by the process wherein 2-phenoxyanthraquinone is used as starting material, the sulfonation is performed by mixing 2-phenoxyanthraquinone with a sulfonating agent in an amount of at least 3 molar proportion to the 2-phenoxyanthraquinone and, if necessary, an inert solvent and heating the mixture. In case 2-phenoxyanthraquinonetetrasulfonates are synthesized by the above process, the sulfonation is performed by heating with a sulfonating agent in an amount of at least 4 molar proportion to the starting material. The heating condition may vary widely according to the sort of sulfonating agent used. For example, the ranges of heating temperature and time in case of using fuming sulfuric acid having a $SO_3$ concentration 0-80% are within 70°-200° C. and 3-20 hours, preferably 100°-180° C. and 5-10 hours and those in case of using sulfur trioxide are within 50°-150° C. and 1-10 hours, preferably 80°-130° C. and 3-8 hours. In this case, the use of an inert solvent is preferable for preventing carbonization of the starting material. The heating temperature and time in case of using chlorosulfonic acid are 100° C. and 10-20 hours, respectively.

Figure 2:
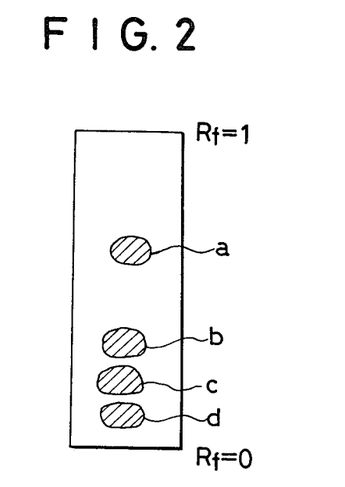
FIG. 2 is a thin layer chromatograph of the reaction liquid in the sulfonation reaction of 2-phenoxyanthraquinone.

On synthesis of the 2-phenoxyanthraquinonepolysulfonates by sulfonation of 2-phenoxyanthraquinone, the proceeding of the reaction can easily be checked by thin layer chromatography of the reaction liquid. FIG. 2 shows a thin layer chromatograph of the reaction liquid when using Spot film silica gel-f (available from Tokyo Kasei KK, Japan) as a thin layer sheet and a mixture of n-butanol-ethanol-0.5 N aqueous ammonia solution (6:2:3 in volume ratio) as a developing liquid.

In FIG. 2, spots (a), (b), (c) and (d) show in the written order spots of 2-phenoxyanthraquinonemonosulfonic acid, 2-phenoxyanthraquinonedisulfonic acid, 2-phenoxyanthraquinonetrisulfonic acid and 2-phenoxyanthraquinonetetrasulfonic acid.

As the sulfonation proceeds, a spot located in the upper position of the thin layer chromatograph becomes smaller while a spot located in the lower position becomes larger. Thus, the end product composed predominantly of 2-phenoxyanthraquinonetrisulfonate can be obtained when the reaction liquid is subjected to a thin layer chromatography and the reaction is deemed as having finished at the stage where the spot (b) almost disappears.

In order to obtain 2-phenoxyanthraquinonetetrasulfonates as end product, the reaction may be deemed as having finished at the stage where the spot (c) of 2-phenoxyanthraquinonetrisulfonic acid disappears. Similarly, mixtures of 2-phenoxyanthraquinonetrisulfonate and 2-phenoxyanthraquinonetetrasulfonate in a variety of proportions are obtained when the end point of the reaction is deemed as a stage where the spot of 2-phenoxyanthraquinonedisulfonic acid disappeared but the spot of 2-phenoxyanthraquinonetrisulfonic acid is still remaining.

In a process wherein 2-phenoxyanthraquinonepolysulfonic acids are synthesized by heating 2-(p-phenoxybenzoyl) benzoic acid with the dehydrating agent and the sulfonating agent, the use of fuming sulfuric acid functioning as both dehydrating agent and sulfonating agent is industrially advantageous.

In this case, the concentration of free $SO_3$ in the fuming sulfuric acid used is within the range from 0% (i.e. 100% sulfuric acid) to 80%. If the concentration is lower than the above range (or in case of using sulfuric acid lower in concentration than 100% sulfuric acid), the sulfonation reaction of 2-phenoxyanthraquinonetrisulfonic acid to 2-phenoxyanthraquinonetetrasulfonic acid will hardly proceed. On the other hand, if the concentration exceeds 80%, handling of such fuming sulfuric acid will become troublesome and side reactions permitting the formation of impurities will tend to take place. For practical operations, the use of such fuming sulfuric acid as having a $SO_3$ concentration of 5-60%, preferably 20-60% is desirable. In this case, the amount of fuming sulfuric acid varies according to the concentration of free $SO_3$ contained therein but the use of fuming sulfuric acid containing 4 molar proportion of free $SO_3$ in preferable for the synthesis of 2-phenoxyanthraquinonetrisulfonates and fuming sulfuric acid containing 5 molar porportion of free $SO_3$ for the synthesis of 2-phenoxyanthraquinonetetrasulfonates. More precisely, 5-100 parts of fuming sulfuric acid is used for 10 parts of 2-(p-phenoxybenzoyl) benzoic acid. Especially, the use of 10-60 parts of fuming sulfuric acid is preferable for convenience of the reaction operations. The reactions are performed by adding 2-(p-phenoxybenzoyl) benzoic acid to the fuming sulfuric acid, gradually elevating the temperature of the mixture with stirring and maintaining the temperature at 100°-200° C. for 1-40 hours, preferably 2-20 hours. The end point of the dehydrocyclizing and sulfonating reactions can be noted by way of a thin layer chromatography or a high speed liquid chromatography of the reaction liquid.

As in the case of the foregoing process wherein 2-phenoxyanthraquinone is used as starting material, the end product composed predominantly of 2-phenoxyanthraquinonetrisulfonic acid is obtained when the end point of the reaction is regarded as the stage where the spot of 2-phenoxyanthraquinonedisulfonic acid in a thin layer chromatograph disappears. Similarly, 2-phenoxyanthraquinonetetrasulfonic acid is obtained when the end point of the reaction is regarded as a stage where the spot of 2-phenoxyanthraquinonetrisulfonic acid disappears. If the reaction is deemed as having finished between the above end points, a mixture of 2-phenoxyanthraquinonetrisulfonate and 2-phenoxyanthraquinonetetrasulfonate is obtained, in which both sulfonates are present in a variable proportion.

Since the 2-phenoxyanthraquinonepolysulfonates possess, as described above, an extremely high solubility to a concentrated aqueous solution of an inorganic salt, it is difficult to isolate the end product in a good yield from the reaction liquid according to a conventional salting-out method. Thus, the isolation of the product is conveniently performed according to the following liming process: The reaction liquid is diluted with water and an alkali metal or ammonium compound such as sodium hydroxide, potassium hydroxide, ammonium hydroxide, sodium sulfate, potassium sulfate, ammonium sulfate or the like salt is added thereto in an amount sufficient to convert the 2-phenoxyanthraquinonepolysulfonic acid formed by the main reaction into a salt thereof. The solution is then neutralized with calcium carbonate or hydroxide and the gypsum thus formed is removed by filtration. The filtrate is concentrated until dryness whereby the 2-phenoxyanthraquinonepolysulfonate aimed at is obtained.

The thus obtained 2-phenoxyanthraquinonepolysulfonate, i.e. 2-phenoxyanthraquinonetrisulfonate, 2-phenoxyanthraquinonetetrasulfonate or a mixture thereof, is commonly a yellow brown solid having no definite melting point which, on ignition, is decomposed.

Figure 3:
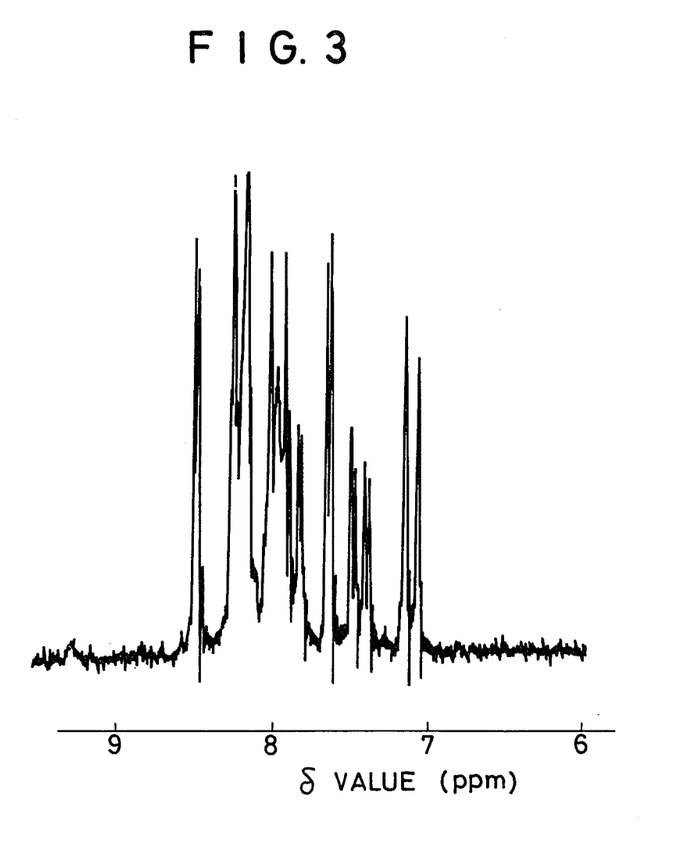
FIGS. 3 and 4 are proton-NMR-absorption spectrographs of sodium 2-phenoxyanthraquinonedisulfonate and sodium 2-phenoxyanthraquinonetetrasulfonate, respectively.

2-phenoxyanthraquinonedisulfonic acid formed as an intermediate product in the course of preparing 2-phenoxyanthraquinonepolysulfonic acid from 2-phenoxyanthraquinone or 2-(p-phenoxybenzoyl) benzoic acid was confirmed, by way of a proton-NMR-absorption spectrum thereof, as having such a structure that the two sulfonic acid groups are bonded, as shown in the reaction formulas (1), to o- and p-positions of the phenoxy group in the 2-phenoxyanthraquinone. FIG. 3 shows a proton-NMR-absorption spectrum (solvent: dimethylacetamide; measuring temp.: room temperature) of sodium 2-phenoxyanthraquinonedisulfonate. This spectrum shows that in the compound of the formula (VII):

absorption of proton f is detected in 8.44 ppm (1H), absorption of protons c, h in 8.04–8.3 ppm (3H), absorption of protons e, g in 7.83–8.02 ppm (3H), absorption of proton a in 7.61 ppm (1H), absorption of proton b in 7.42 ppm (1H) and absorption of proton d in 7.1 ppm (1H). It is confirmed therefore that 2-phenoxyanthraquinonedisulfonic acid has the structure shown by the formula (VII). The structure of the formula (VII) is supported also by the fact that when this 2-phenoxyanthraquinonedisulfonic acid is treated under heating with a 5% aqueous solution of sodium hydroxide, the phenoxy group of this compound is split off to afford 2-hydroxyanthraquinone.

Figure 4:
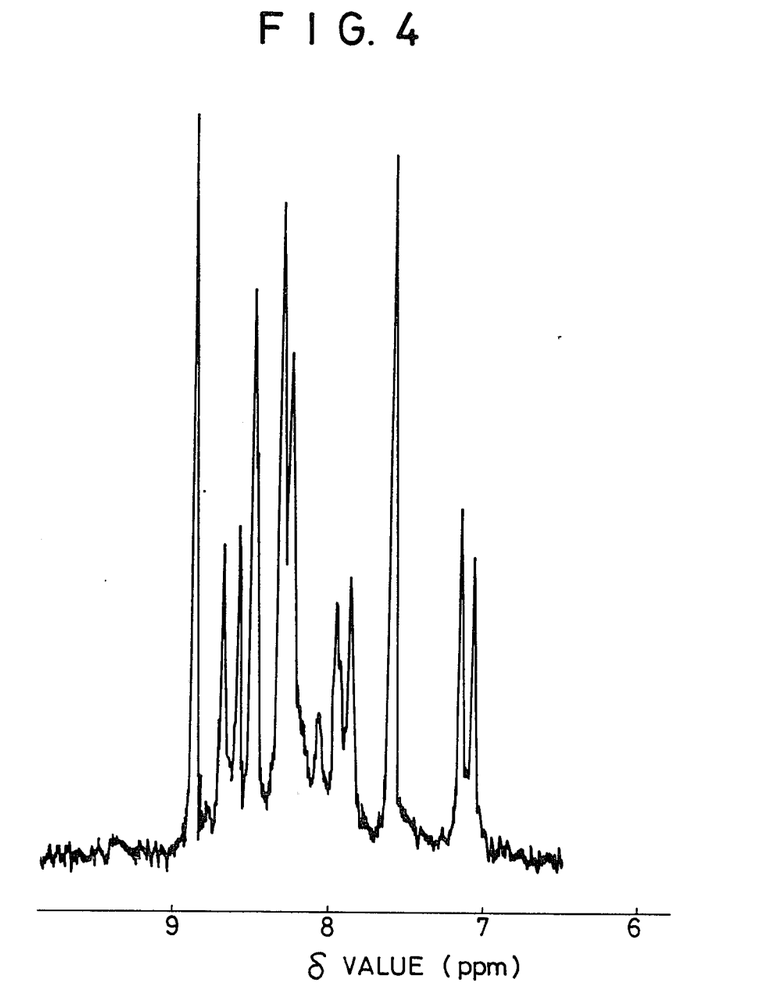
Figure 5:
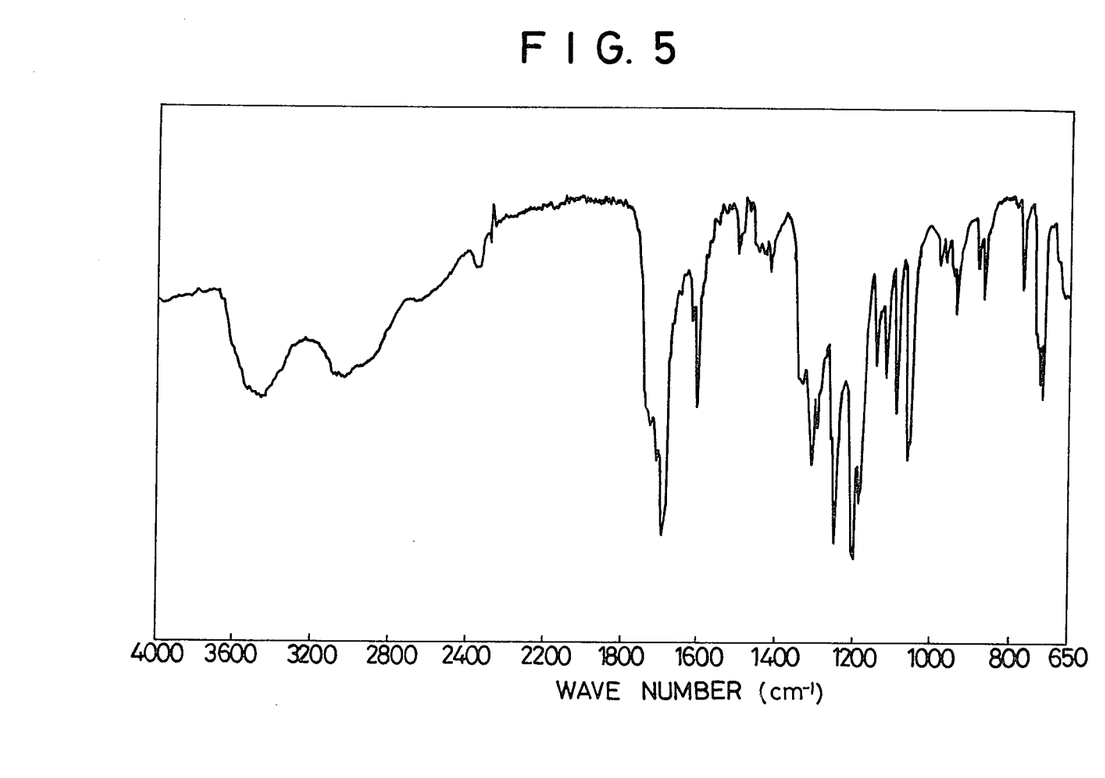
FIGS. 5, 6 and 7 are IR-absorption spectrographs of sodium 2-carboxyanthraquinonemonosulfonate, sodium 2-phenoxyanthraquinonetetrasulfonate and sodium 2-phenoxyanthraquinonetrisulfonate, respectively.
Figure 6:
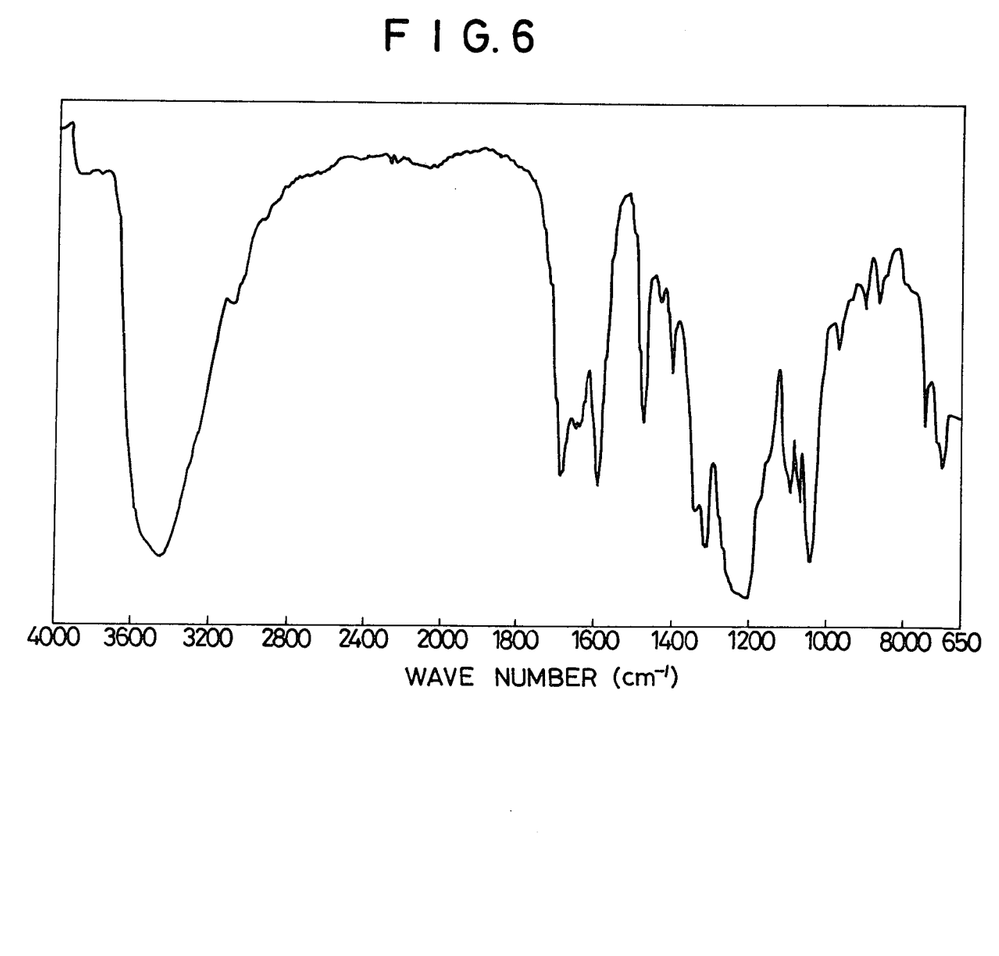
Figure 7:
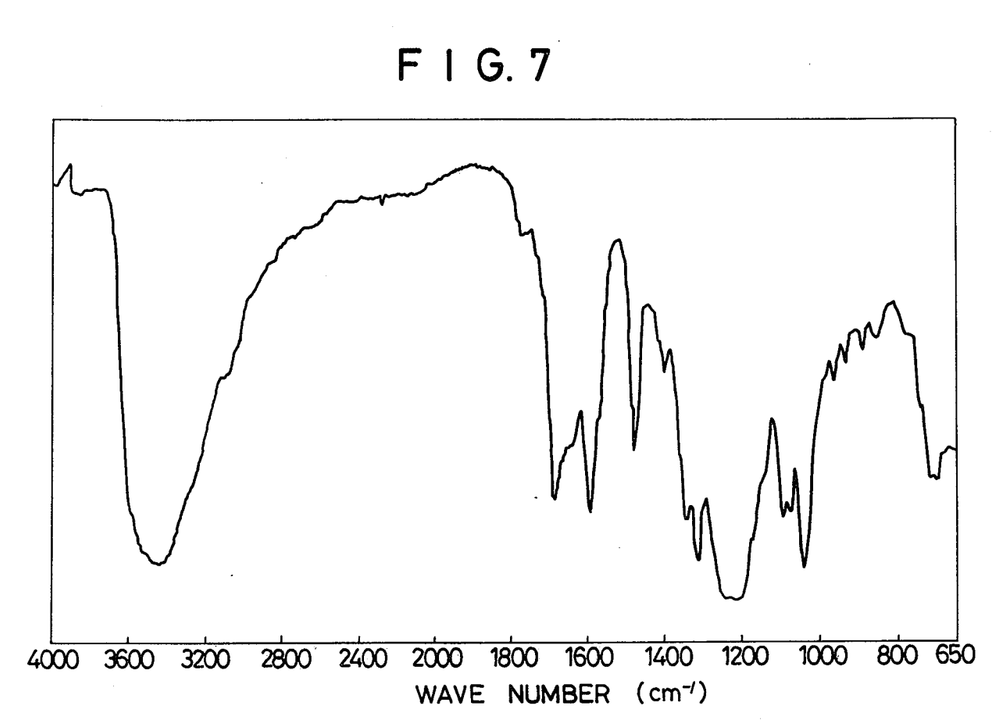

Sodium 2-phenoxyanthraquinonetetrasulfonate of this invention is a mixture of two isomers having the structures shown by the formulas (VIII) and (IX):

This fact is corroborated by a proton-NMR-absorption spectrum (solvent: dimethylacetamide; mesuring temp.: room temperature) of sodium 2-phenoxyanthraquinonetetrasulfonate given in FIG. 4 which shows that in the compounds of the formulas (VIII) and (IX), absorption of proton b is detected in 8.84 ppm (1H), absorption of proton f in 8.66 ppm and 8.56 ppm (1H), absorption of proton e in 8.45 ppm (1H), absorption of protons g, h in 8.2–8.4 ppm (2H), absorption of proton d in 7.9 ppm (1H), absorption of proton a in 7.56 ppm (1H) and absorption of proton c in 7.1 ppm (1H).

It is evident from results of elementary analysis shown in the Examples that 2-phenoxyanthraquinonetrisulfonates contain 3 sulfonate groups per molecule and can thus be shown by the formula (V). Taking the structures of 2-phenoxyanthraquinonedisulfonic acid and 2-phenoxyanthraquinonetetrasulfonic acid also into consideration, 2-phenoxyanthraquinonetrisulfonates have such a structure that 2 sulfonate groups out of the three sulfonate groups are bonded to o and p-positions of the phenoxy group and the remaining one sulfonate group is bonded to 3-, 6- or 7-position of the anthraquinone nucleus.

Noteworthy here is that sodium 2-phenoxyanthraquinone-2',4'-disulfonate of the formula (VII) possesses a significantly high solubility but is found substantially to be unsuited for use in the Stretford process notwithstanding this compound has the anthraquinone nucleus susceptible of reversible oxidation-reduction. In practical use, this compound is inferior in the oxidation efficiency of hydrogen sulfide to elemental sulfur and also in the capturing rate for hydrogen sulfide. This may be ascribable to the fact that the standard oxidation-reduction potential of the sodium disulfonate is a somewhat low value of 0.21 V. From this fact, it is understood that anthraquinone compounds having good solubility are not necessarily suitable as oxidation-reduction reagents for the Stretford process since the oxidation-reduction characteristics of the anthraquinone compounds are delicately influenced by the sort, position and number of substituents and that it is quite impossible to anticipate the excellent effect of the oxidation-reduction reagents of this invention from similar compounds.

This invention will now be illustrated in more detail by way of examples in which parts and percentages are by weight. It is to be construed however that the invention is not limited by such specific embodiments.

EXAMPLE 1

To 288 parts of 25% fuming sulfuric acid were added 81 parts of benzophenone-2,4-dicarboxylic acid and 42.6 parts of anhydrous sodium sulfate. The mixture was heated under agitation up to 180° C. in 3 hours and maintained at this temperature for 6 hours to effect cyclization-sulfonation reactions. After cooling the reaction mixture to room temperature, the reaction mixture was poured into 1200 parts of water and the whole was stirred for one hour. The precipitate was collected by filtration and washed with 600 parts of a 10% aqueous solution of sodium sulfate and the filter cake was then dried whereby 116 parts of sodium 2-carboxyanthraquinonemonosulfonate was obtained.

EXAMPLE 2

To 150 parts of 50% fuming sulfuric acid were added 81 parts of benzophenone-2,4-dicarboxylic acid and 52.5 parts of anhydrous potassium sulfate. The mixture was heated under agitation up to 160° C. in 4 hours and maintained at this temperature for 6 hours to effect cyclization-sulfonation reactions. After cooling the reaction mixture to room temperature, the reaction mixture was poured into 1200 parts of water and the whole was stirred for one hour. The precipitate was collected by filtration and washed with 600 parts of a 10% aqueous solution of sodium sulfate and the filter cake was dried whereby 119 parts of sodium 2-carboxyanthraquinonemonosulfonate was obtained.

EXAMPLE 3

To 288 parts of 25% fuming sulfuric acid was added 81 parts of benzophenone-2,4-dicarboxylic acid. The mixture was heated under agitation up to 180° C. in 3 hours and maintained at this temperature for 6 hours to effect cyclization-sulfonation reactions. After cooling the reaction mixture to room temperature, the reaction mixture was poured into 1200 parts of 10% aqueous solution of ammonium sulfate and the whole was stirred for one hour. The precipitate was collected by filtration and washed with 600 parts of a 10% aqueous solution of ammonium sulfate and the filter cake was dried whereby 110 parts of ammonium 2-carboxyanthraquinonemonosulfonate was obtained.

EXAMPLE 4

Except that 81 parts of a mixture (1:1) of benzophenone-2,4-dicarboxylic acid and benzophenone-2,5-dicarboxylic acid was used in place of benzophenone-2,4-dicarboxylic acid described in Example 1, the same operation as described in Example 1 was repeated whereby 112 parts of sodium 2-carboxyanthraquinonemonosulfonate was obtained.

EXAMPLE 5

Except that 81 parts of 2-(p-carboxybenzoyl) benzoic acid was used in place of benzophenone-2,4-dicarboxylic acid described in Example 1, the same operation as described in Example 1 was repeated whereby 115 parts of 2-carboxyanthraquinonemonosulfonate was obtained.

EXAMPLE 6

To 44 parts of 54.5% fuming sulfuric acid in which free $SO_3$ was 6 molar proportion to 2-(p-phenoxybenzoyl) benzoic acid were added 15.9 parts of 2-(p-phenoxybenzoyl) benzoic acid and 7.1 parts of anhydrous sodium sulfate. The mixture was heated under agitation up to 180° C. in 3 hours and maintained at this temperature for 4 hours to effect cyclization-sulfonation reactions until the spot of 2-phenoxyanthraquinonetrisulfonic acid disappeared when a part of the reaction liquid was occasionally subjected to a thin layer chromatography. After cooling the reaction mixture to room temperature, the reaction mixture was poured into 100 parts of water and 5 parts of caustic soda were added to the aqueous solution under vigorous agitation. Calcium carbonate was then added to the solution until it became neutral while maintaining the temperature at 70°-80° C. whereby gypsum was precipitated. The mixture was filtered and the filtrate was subjected to spray drying whereby 34 parts of yellow brown powders were obtained, which showed no definite melting point and was decomposed on ignition. A result of an elementary analysis of the product purified by extracting the yellow brown powders with methanol was well in agreement with a calculated value based on the composition of sodium 2-phenoxyanthraquinonetetrasulfonate tetrahydrate ($C_{20}H_{16}O_{19}S_4Na_4$) as follows:

A result of elementary analysis: Found: C, 31.55%; H, 1.87%; S, 16.47%. Calc.: C, 30.78%; H, 2.05%; S, 16.43%.

FIG. 4 shows a proton-NMR-absorption spectrum of this compound.

EXAMPLE 7

To 66.7 parts of 30% fuming sulfuric acid in which free $SO_3$ was 5 molar proportion to 2-phenoxyanthraquinone were added 15 parts of 2-phenoxyanthraquinone and 10.7 parts of anhydrous sodium sulfate. The mixture was heated under agitation up to 180° C. in 10 hours and maintained at this temperature for 3 hours to effect sulfonation reaction until the spot of 2-phenoxyanthraquinonetrisulfonic acid disappeared when a part of the reaction liquid was occasionally subjected to a thin layer chromatography. After cooling the reaction mixture to room temperature, the reaction mixture was poured into 200 parts of water and 3 parts of caustic soda was added to the aqueous solution under vigorous agitation. Calcium hydroxide was then added to the solution until it became neutral while maintaining the temperature at 70°-80° C. whereby gypsum was precipitated. The mixture was then filtered and the filtrate was subjected to spray drying whereby 33 parts of sodium 2-phenoxyanthraquinonetetrasulfonate in the form of yellow brown powders were obtained. The product purified by extracting the yellow brown powders with methanol was similar in data of elementary analysis, IR-absorption spectrum and proton-NMR-absorption spectrum to sodium 2-phenoxyanthraquinonetetrasulfonate obtained in Example 4.

EXAMPLE 8

Except that 13 parts of anhydrous potassium sulfate and 4 parts of caustic potash were used in place of the anhydrous sodium sulfate and caustic soda described in Example 7, the reaction was carried out in the same manner as described in Example 7 whereby 35 parts of potassium 2-phenoxyanthraquinonetetrasulfonate were obtained.

Except that 30 parts of conc. ammonia water were used in place of the caustic soda described in Example 7, the reaction was carried out in the same manner as described in Example 7 whereby 33 parts of ammonium 2-phenoxyanthraquinonetetrasulfonate were obtained.

EXAMPLE 9

To 33 parts of 52% fuming sulfuric acid in which free $SO_3$ was 4.3 molar proportion to 2-(p-phenoxybenzoyl) benzoic acid were added 15.9 parts of 2-(p-phenoxybenzoyl) benzoic acid and 7.1 parts of anhydrous sodium sulfate. The mixture was heated under agitation up to 180° C. in 3 hours and maintained at this temperature for 7 hours to effect cyclization-sulfonation reactions until the spot of 2-phenoxyanthraquinonedisulfonic acid disappeared when a part of the reaction liquid was occasionally subjected to a thin layer chromatography. After cooling the reaction mixture to room temperature, the reaction mixture was poured into 100 parts of water and 3 parts of caustic soda were added to the aqueous solution under vigorous agitation.

Calcium carbonate was then added to the aqueous solution until it became neutral while maintaining the temperature at 70°-80° C. whereby the gypsum was precipitated. The mixture was then filtered and the filtrate was subjected to spray drying whereby 30.5 parts of yellow brown powders were obtained, which showed no definite melting point and was decomposed on ignition. A result of an elementary analysis of the product purified by extracting the yellow brown powders with methanol was well in agreement with a calculated value based on the composition of sodium 2- phenoxyanthraquinonetrisulfonate trihydrate ($C_{20}H_{15}O_{15}S_3Na_3$) as follows:

A result of elementary analysis: Found: C, 36.13%; H, 2.11%; S, 14.42%. Calc.: C, 36.37%; H, 2.29%; S, 14.56%.

EXAMPLE 10

To 47 parts of 30% fuming sulfuric acid in which free $SO_3$ was 3.5 molar proportion to 2-phenoxyanthraquinone were added 15 parts of 2-phenoxyanthraquinone and 10.7 parts of anhydrous sodium sulfate. The mixture was heated under agitation up to 180° C. in 10 hours and kept at this temperature for 3 hours to effect sulfonation reaction until the spot of 2-phenoxyanthraquinonedisulfonic acid almost disappeared when a part of the reaction liquid was occasionally subjected to a thin layer chromatography.

After cooling the reaction mixture to room temperature, the reaction mixture was poured into 200 parts of water and 2 parts of caustic soda were added to the aqueous solution under vigorous agitation. Calcium carbonate was then added to the aqueous solution until it became neutral while maintaining the temperature at 70°–80° C. whereby gypsum was precipitated. The mixture was then filtered and the filtrate was subjected to spray drying whereby 30.2 parts of sodium 2-phenoxyanthraquinonetrisulfonate in the form of yellow brown powders were obtained.

The product purified by extracting the yellow brown powders with methanol was similar in data of elementary analysis and IR-absorption spectrum to sodium 2-phenoxyanthraquinonetrisulfonate obtained in Example 9.

EXAMPLE 11

An absorption column was prepared by charging a glass tube (with a jacket) of 10 cm in inner diameter and 100 cm in length with a basket type filler of polypropylene (Tellerette S available from Nittetsu Kakoki KK, Japan) with a diameter of 1 cm up to a height of 95 cm. A hydrogen sulfide-containing gas prepared by mixing a gas composed of 6% carbon dioxide and 94% nitrogen with hydrogen sulfide in an amount of 5 $g/Nm^2$ was introduced at a flow rate of 230 l/hr. into the absorption column from the bottom thereof. On the other hand, an alkaline aqueous solution containing 0.03 mol/l of sodium metavanadate and 0.005 mol/l of sodium 2-carboxyanthraquinonemonosulfonate, which had been adjusted to have a pH value of 9 by addition of sodium carbonate and was kept at 40° C. was sprayed at a rate of 4.6 l/hr. into the absorption column from the top thereof whereby the hydrogen sulfide-containing gas was brought in the column into contact with the alkaline aqueous solution.

A gas/liquid ratio in this case was 0.02. From the lower part of the absorption column, the liquid was discharged and conveyed into a regeneration column made of a glass tube (with a jacket) of 10 cm in inner diameter and 100 cm in length where elementary sulfur was completely precipitated from the liquid by blowing air thereinto. A residence time of the liquid in the regeneration column was 20 minutes.

By treating the hydrogen sulfide-containing gas in such manner, hydrogen sulfide in the gas could be eliminated at a desulfurization ratio of 99.7% or more. The quantity of sulfur recovered from the regeneration column corresponded to 97% of hydrogen sulfide contained in the feed gas.

When the hydrogen sulfide-containing gas was treated in the same manner as described above except that sodium anthraquinone-2,7-disulfonate was used in place of sodium 2-carboxyanthraquinonemonosulfonate, the desulfurization ratio obtained was 99.6%.

EXAMPLE 12

When the treatment was carried out in the same manner as described in Example 11 except that potassium 2-carboxyanthraquinonemonosulfonate or ammonium 2-carboxyanthraquinonemonosulfonate was used in place of sodium 2-carboxyanthraquinonemonosulfonate, hydrogen sulfide in the hydrogen sulfide-containing gas could be eliminated in each case at a desulfurization ratio of at least 99.7%.

EXAMPLE 13

An absorption column was prepared by charging a glass tube (with a jacket) of 10 cm in inner diameter and 100 cm in length with a basket type filler of polypropylene (Tellerette S) with a diameter of 1 cm up to a height of 95 cm. A hydrogen sulfide-containing gas prepared by mixing a gas composed of 6% carbon dioxide and 94% nitrogen with hydrogen sulfide in an amount of 5 $g/Nm^3$ was introduced at a flow rate of 230 l/hr. into the absorption column from the bottom thereof. On the other hand, an alkaline aqueous solution containing 0.03 mol/l of sodium metavanadate and 0.005 mol/l of sodium 2-phenoxyanthraquinonetrisulfonate, which had been adjusted to have a pH value of 9 by addition of sodium carbonate and was kept at 40° C. was sprayed at a rate of 4.6 l/hr. into the absorption column from the top thereof whereby the hydrogen sulfide-containing gas was brought in the column into contact with the alkaline aqueous solution. A gas/liquid ratio in this case was 0.02. From the lower part of the absorption column, the liquid was discharged and conveyed into a regeneration column made of a glass tube (with a jacket) of 10 cm in inner diameter and 100 cm in length where elementary sulfur was completely precipitated from the liquid by blowing air thereinto. A residence time of the liquid in the regeneration column was 20 minutes.

By treating the hydrogen sulfide-containing gas in such manner, hydrogen sulfide in the gas could be eliminated at a desulfurization ratio of 99.7% or more. The quantity of sulfur recovered from the regeneration column corresponded to 97% of hydrogen sulfide contained in the feed gas.

EXAMPLE 14

When the treatment was carried out in the same manner as described in Example 13 except that sodium 2-phenoxyanthraquinonetetrasulfonate or a mixture (1:1 in weight ratio) of sodium 2-phenoxyanthraquinonetrisulfonate and sodium 2-phenoxyanthraquinonetetrasulfonate was used in place of sodium 2-phenoxyanthraquinonetrisulfonate, hydrogen sulfide in the hydrogen sulfide-containing gas could be eliminated in each case at a desulfurization ratio of at least 99.7%.

EXAMPLE 15

When the treatment was carried out in the same manner as described in Example 13 except that potassium 2-phenoxyanthraquinonetrisulfonate, potassium 2-phenoxyanthraquinonetetrasulfonate or ammonium 2-phenoxyanthraquinonetetrasulfonate was used in place of sodium 2-phenoxyanthraquinonetrisulfonate, hydrogen sulfide in the hydrogen sulfide-containing gas could be eliminated in each case at a desulfurization ratio of at least 99.7%.

EXAMPLE 16

An absorption column was prepared by charging a glass tube (with a jacket) of 10 cm in inner diameter and 100 cm in length with a basket type filler of polypropylene (Tellerett S) with a diameter of 1 cm up to a height of 95 cm. A hydrogen sulfide-containing gas prepared by mixing a gas composed of 6% carbon dioxide and 94% nitrogen with hydrogen sulfide in an amount of 5 g/Nm$^3$ was introduced at a flow rate of 250 l/hr. into the absorption column from the bottom thereof. On the other hand, an alkaline aqueous solution containing 0.03 mol/l of sodium metavanadate, 0.0025 mol/l of sodium 2-carboxyanthraquinonemonosulfonate and 0.0025 mol/l of sodium anthraquinone-2,7-disulfonate, which had been adjusted to have a pH value of 9 by addition of sodium carbonate and was kept at 40° C. was sprayed at a rate of 4.6 l/hr. into the absorption column from the top thereof whereby the hydrogen sulfide-containing gas was brought in the column into contact with the alkaline aqueous solution.

A gas/liquid ratio in this case was 0.02. From the lower part of the absorption column, the liquid was discharged and conveyed into a regeneration column made of a glass tube (with a jacket) of 10 cm in inner diameter and 100 cm in length where elementary sulfur was completely precipitated from the liquid by blowing air thereinto. A residence time of the liquid in the regeneration column was 20 minutes.

By treating the hydrogen sulfide-containing gas in such manner, hydrogen sulfide in the gas could be eliminated at a desulfurization ratio of 99.7% or higher.

The quantity of sulfur recovered from the regeneration column corresponded to 97% of hydrogen sulfide contained in the feed gas.

EXAMPLE 17

When the treatment was carried out in the same manner as described in Example 13 except that sodium 2-carboxyanthraquinonetetrasulfonate or sodium 2-phenoxyanthraquinonetrisulfonate was used in place of sodium 2-carboxyanthraquinonemonosulfate, hydrogen sulfide in the hydrogen sulfide-containing gas could be eliminated in each case at a desulfurization ratio of at least 99.7%.

What is claimed is:

1. A composition containing an oxidation-reduction reagent for a wet desulfurization process, which comprises: (a) an alkaline aqueous solution of at least about 0.1% of one or more compounds selected from the group consisting of salts of substituted anthraquinone-sulfonic acids of the general formulae wherein M stands for a sodium atom, a potassium atom or an ammonium group and n is an integer of 1 or 2; (b) sodium metavanadate of 1/1000–1/20 mol per liter of said aqueous solution; and (c) a sufficient amount of sodium carbonate to make the pH value of said aqueous solution range from 8.5 to 9.5.

2. The composition as in claim 1 wherein said oxidation-reduction reagent is sodium, potassium or ammonium 2-carboxy-anthraquinone-6 or 7-sulfate.

3. The composition as in claim 1 wherein said wet desulfurization process is the "Stretford process".

4. The composition as in claim 1, wherein said oxidation-reduction reagent comprises (a) at least one compounds selected from the group consisting of salts of substituted anthraquinone-sulfonic acids of the general formulae

* * * * *